United States Patent
Tsukui et al.

(10) Patent No.: US 6,805,843 B2
(45) Date of Patent: Oct. 19, 2004

(54) SLIDE GLASS RACK FOR USE IN CENTRIFUGAL APPARATUS

(75) Inventors: Sadashi Tsukui, Tokyo-to (JP); Masami Arakawa, Miyoshi-Machi (JP)

(73) Assignee: Tomy Kogyo Co., Ltd, Wako (JP)

(*) Notice: Subject to any disclaimer, the term of this patent is extended or adjusted under 35 U.S.C. 154(b) by 0 days.

(21) Appl. No.: 09/987,546

(22) Filed: Nov. 15, 2001

(65) Prior Publication Data

US 2003/0013589 A1 Jan. 16, 2003

(30) Foreign Application Priority Data

Jul. 10, 2001 (JP) ........................................ 2001-209796

(51) Int. Cl.[7] .................................................. B01L 3/00
(52) U.S. Cl. ...................................... 422/102; 422/104
(58) Field of Search ................................ 422/102, 104, 422/82.05; 356/244, 246; 494/16, 20

(56) References Cited

U.S. PATENT DOCUMENTS

| | | | | |
|---|---|---|---|---|
| 4,089,989 A | * | 5/1978 | White et al. | ............... 427/2.11 |
| D256,470 S | * | 8/1980 | Gordon | ....................... D16/50 |
| 4,250,830 A | * | 2/1981 | Leif | ............................. 118/52 |
| 4,344,562 A | * | 8/1982 | Ricci | ........................... 494/20 |
| 4,349,275 A | * | 9/1982 | Ayotte et al. | ................ 356/36 |
| 4,501,495 A | * | 2/1985 | Faulkner et al. | ............ 356/244 |
| 4,801,431 A | * | 1/1989 | Cuomo et al. | .............. 422/104 |
| 4,853,188 A | * | 8/1989 | Toya | ......................... 427/2.11 |
| 4,874,582 A | * | 10/1989 | Gordon et al. | .............. 422/102 |
| 5,021,218 A | * | 6/1991 | Davis et al. | ................. 422/104 |
| 5,180,606 A | * | 1/1993 | Stokes et al. | ............... 427/2.13 |
| 5,781,337 A | * | 7/1998 | Pfeifer | ........................ 359/391 |
| 6,309,362 B1 | * | 10/2001 | Guirguis | ...................... 600/573 |

\* cited by examiner

Primary Examiner—Jeffrey Snay
(74) Attorney, Agent, or Firm—Vardnell & Vardnell, PLLC

(57) ABSTRACT

A slide glass rack for use in a centrifugal apparatus has a slide glass accommodating concave that opens upward, and a flange provided on an upper outer peripheral surface of the rack. A centrifugal apparatus that uses the slide glass rack comprises a rotor, wherein the rotor is formed at a peripheral edge thereof with an inclined face extending upward obliquely with a predetermined angle, the inclined face being formed with a rectangular hole through which a slide glass rack is inserted, the flange of the rack is supported by the peripheral edges of the rectangular hole.

2 Claims, 5 Drawing Sheets

SLIDE GLASS RACK FOR USE IN CENTRIFUGAL APPARATUS

FIELD OF THE INVENTION AND RELATED ART STATEMENT

The present invention relates to a slide glass rack for use in a centrifugal apparatus and a centrifugal apparatus suited for performing centrifugal operations to a specimen placed on a slide glass.

In the DNA microarray technology, for example, inspection of DNA is generally conducted on a specimen that is attached to a slide glass. Since the inspection accuracy is influenced by the conditions of the surface of the slide glass, a centrifugal apparatus is employed to remove the reagents used in coating to the slide glass, DNA hybridization processes or to dry the slide glass to improve the surface conditions of the slide glass.

In such a conventional centrifugal apparatus, slide glasses are directly held by a rotor of the apparatus to perform the centrifugal operations. As a result, water (liquid) blown off from the slide glass is accumulated inside a chamber of the apparatus. Therefore, it is necessary for the apparatus to be structured so that the accumulated water (liquid) is discharged outside, which makes the structure of the apparatus complicated and may increase the size of the apparatus.

OBJECT AND SUMMARY OF THE INVENTION

Accordingly, an object of the present invention is to provide a slide glass rack for a centrifugal apparatus capable of dewatering a specimen placed on a slide glass during centrifugal operations, with no necessity of using a centrifugal apparatus of specially designed structure.

According to the first aspect of the invention, a slide glass rack for use in a centrifugal apparatus having a slide glass accommodating concave that opens upward, and a flange provided on an upper outer peripheral surface of the rack.

A slide glass rack of the present invention is used in a state where it is mounted on the rotor of a centrifugal apparatus. In this slide glass rack of the present invention, water (liquid) blown off by the centrifugal force is accumulated in the concave for accommodating a slide glass. As a result, since the water (liquid) blown off by the centrifugal force is not led and accumulated into the chamber of the apparatus, it is not necessary to provide a liquid discharging device for the chamber of the apparatus, which makes the structure of the centrifugal apparatus simple.

According to the second aspect of the present invention, in the slide glass rack of the first aspect of the present invention, the slide glass accommodating concave has opposing ends, each of the opposing ends formed with a gap that is slightly larger than thickness of a slide glass, for positioning and supporting the slide glass, whereby the slide glass is held in the slide grass accommodating concave in such a manner that surfaces of a middle portion of the slide glass are separated from side walls defining the slide grass accommodating concave.

With the slide glass rack of this configuration, the slide glass is positioned and supported at the opposing ends thereof. Therefore, the middle portion of the slide glass where a specimen of DNA is attached can be sufficiently separated from the side walls of the concave of the rack.

According to the third aspect of the present invention, in the slide glass rack of the first aspect of the present invention, side walls defining the opposing ends of the slide glass accommodating concave is cut out at upper portions thereof, whereby a part of opposing ends of the slide glass held in the slide glass accommodating concave is exposed through the cutout portions.

With the slide glass rack of this configuration, the opposing end portions of the slide glass are exposed through the cut-out portion, and the slide glass can be easily taken out from the rack by picking up the exposed opposing end portions with fingers. Thus, taking out of the slide glass from the rack is easily done while the fingers are not in touch with the specimen placed in the middle of the slide glass.

According to the fourth aspect of the present invention, in the slide glass rack of the first aspect of the invention, a corner portion where outer surface of a side wall defining a longitudinal end of the rack and outer surface of a bottom wall of the rack meet is formed with an arc-shaped surface or an inclined plane surface.

With the slide glass rack of this configuration, the outer corner portions thereof do not extend outwardly. Therefore, when the rack is mounted in the rotor and is rotated, the rotation trajectory becomes smaller. As a result, the centrifugal apparatus can be smaller in size.

According to the fifth aspect of the present invention, in the slide glass rack of the first aspect of the invention, a corner portion where inner surface of a side wall defining a longitudinal end of the rack and inner surface of a bottom wall of the rack meet is formed with an arc-shaped surface or an inclined plane surface in such a manner as to deviate, toward the bottom wall, outside of a plane that is perpendicular to a direction in which centrifugal force is directed.

With the slide glass rack of this configuration, water (liquid) scattered by centrifugal force flows along the inner side wall surfaces, round surfaces or inclined surfaces of the rack that define the slide glass accommodating concave, and reaches the bottom wall of the rack. Thus, the water (liquid) is reliably guided and accumulated in the bottom of the concave.

According to the sixth aspect of the present invention, in the slide glass rack of the first aspect of the invention, a bottom wall defining the slide glass accommodating concave is provided with a rib that extends upward from the bottom wall to support a lower end face of a slide glass.

With the slide glass rack of this configuration, the slide glass is placed in the slide glass accommodating concave with a sufficient space from the bottom wall of the concave. Therefore, such a situation cannot occur in which the slide glass is immersed into the accumulated water (liquid).

According to the seventh aspect of the present invention, in the slide glass rack of the invention, the rib is formed integrally with one of side walls defining the slide glass accommodating concave while a gap is provided between the rib and another of the side walls.

With the slide glass rack of this configuration, the bottom portion of the slide glass accommodating concave is not divided into portions because of the space between the rib and the other side wall. Thus, water (liquid) accumulated in the bottom portion is uniformly distributed without being disturbed by the rib.

According to the eighth aspect of the present invention, a centrifugal apparatus comprises a rotor, wherein the rotor is formed at a peripheral edge thereof with an inclined face extending upward obliquely with a predetermined angle, the inclined face being formed with a rectangular hole through which a slide glass rack is inserted.

With the centrifugal apparatus of this configuration, the peripheral edge of the hole provided in the rotor receives the flange of the rack and holds the rack. Thus, the rotor can be of a simple structure, inexpensive and small.

According to the ninth aspect of the present invention, in the centrifugal apparatus of the eighth aspect of the invention, the rotor is formed by a plate.

With the centrifugal apparatus of this configuration, by defining a rotor by a plate, the centrifugal apparatus can be inexpensive.

DETAILED DESCRIPTION OF PREFERRED EMBODIMENT

Figure 1:
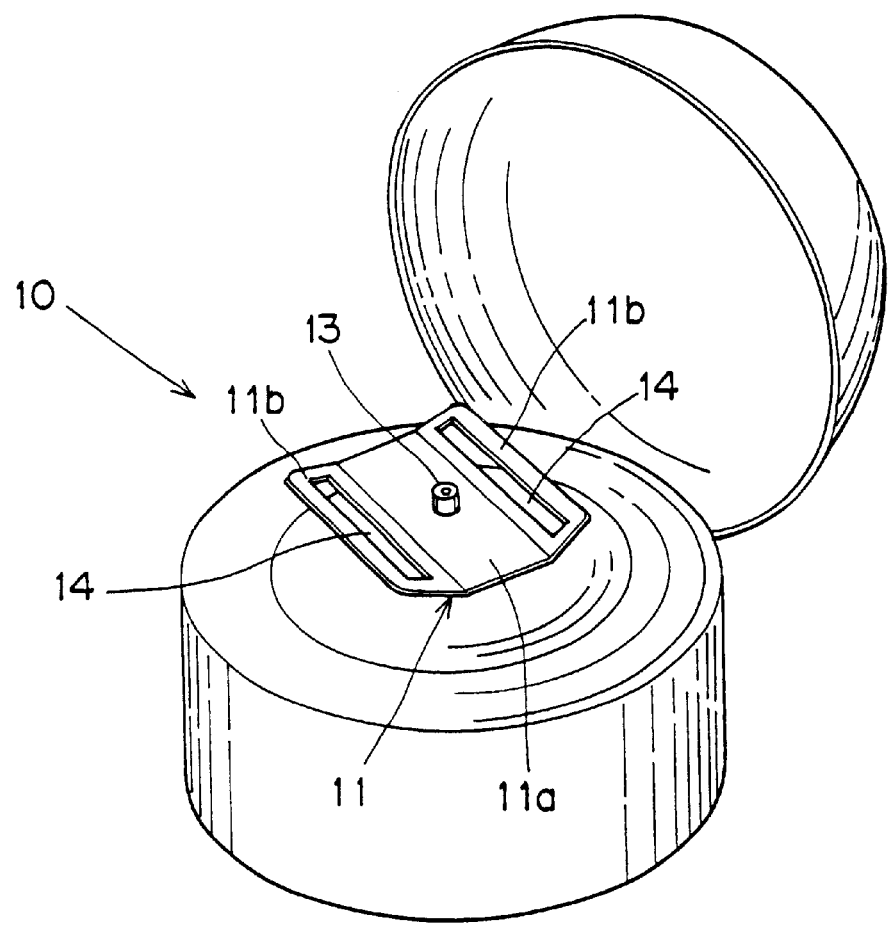
FIG. 1 is a perspective view illustrating an embodiment of the centrifugal apparatus according to the present invention.
Figure 2:
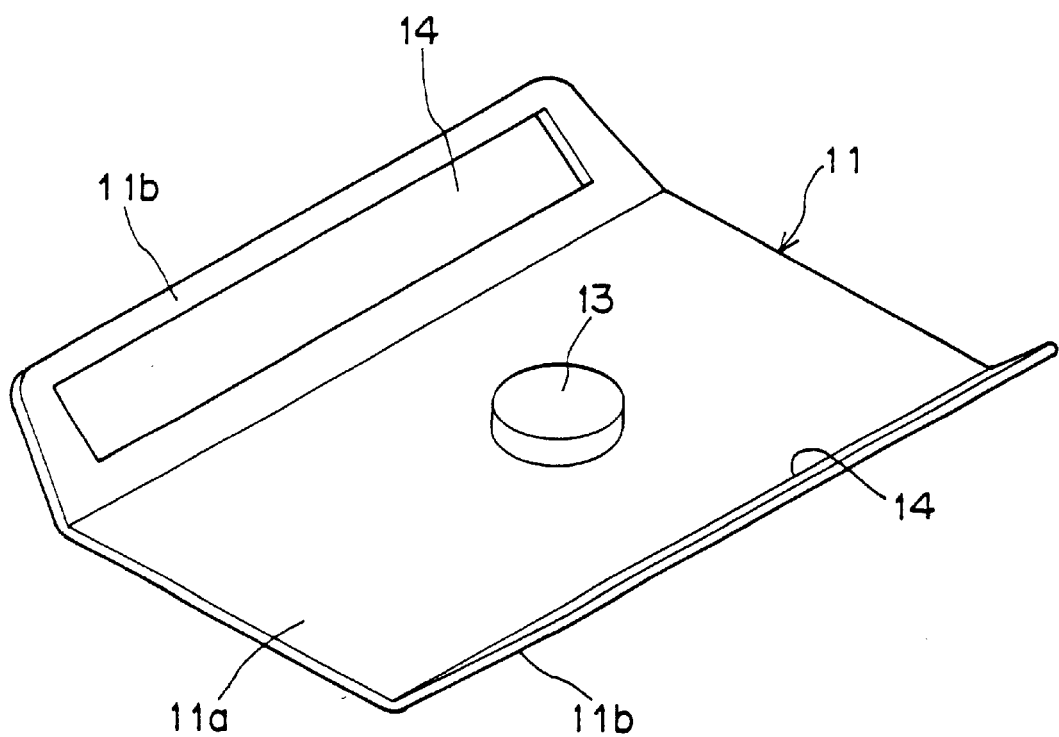
FIG. 2 is a perspective view illustrating a rotor of the centrifugal apparatus of FIG. 1.
Figure 7:
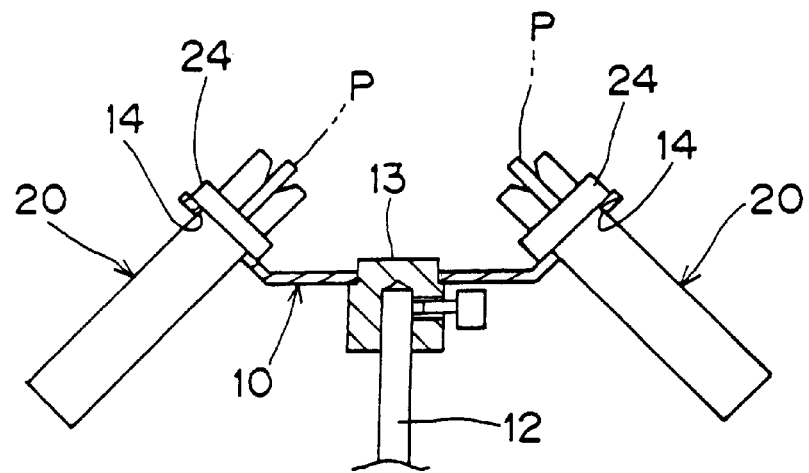
FIG. 7 is a sectional view illustrating the rotor of FIG. 1 with the slide glass rack being mounted thereon.

Referring to FIGS. 1 and 2, a centrifugal apparatus 10 according to an embodiment of the present invention is characterized in the configuration of a rotor 11. The rotor 11 is made, for example, of a steel plate having a rectangular shape and thickness of 1.2 mm. The rotor 11 extends perpendicular to a drive shaft 12 (FIG. 7), and comprises a plate 11a of rectangular shape provided at the center thereof with a boss 13 that is secured to the drive shaft 12, and inclined portions 11b extending upward obliquely from opposing sides of the plate 11a with an angle, for example, of 45 degree. The inclined portions are respectively provided with a rectangular hole 14 having, for example, 82.4×9.8 mm in size, through which a slide glass rack 20 for a slide glass P is inserted as described later.

Figure 3:
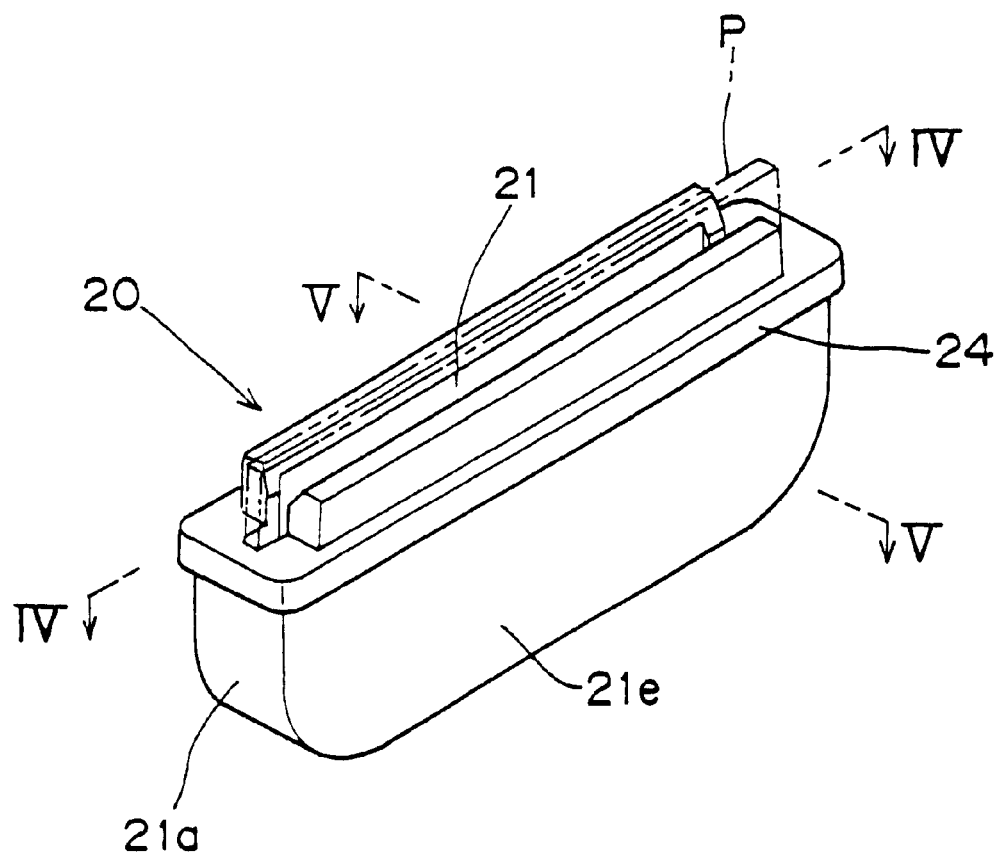
FIG. 3 is a perspective view illustrating a slide glass rack for use in a centrifugal apparatus according to the present invention.

Referring to FIG. 3, the slide glass rack 20 is made of transparent synthetic resin such as polycarbonate, and is integrally formed in substantially rectangular parallelepiped shape having a size larger than the slide glass P, whose thickness, length and width are, for example, 1.1×76.2×25.4 mm. The rack 20 has a slide grass accommodating concave 21 that is open upwardly.

Figure 4:
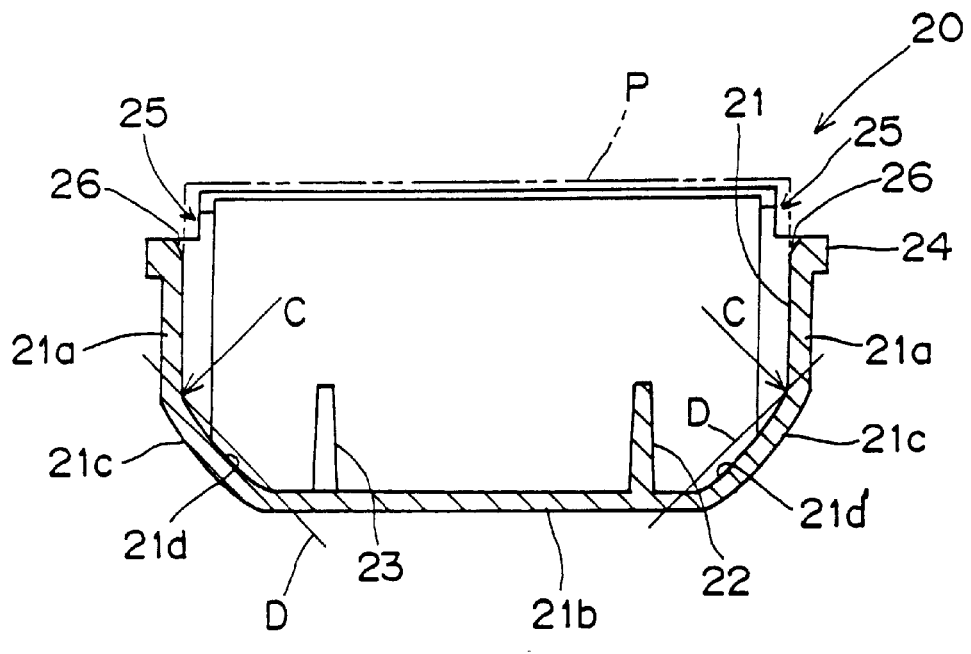
FIG. 4 is a sectional view of the slide glass rack taken along the line IV—IV of FIG. 3.
Figure 5:
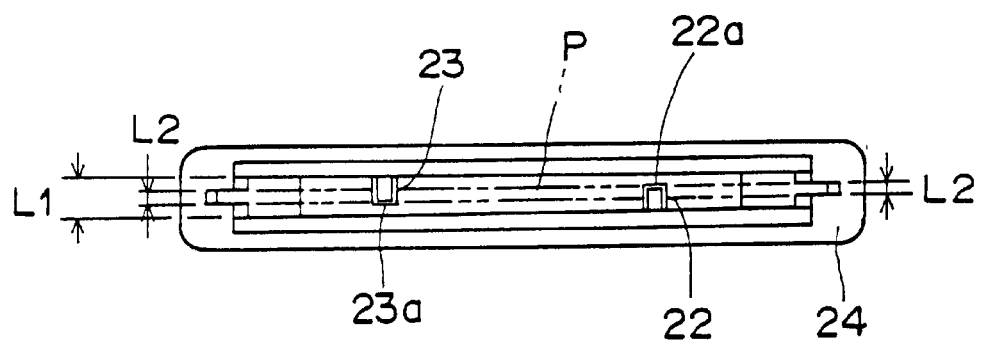
FIG. 5 is a plan view of the slide glass rack of FIG. 3.
Figure 6:
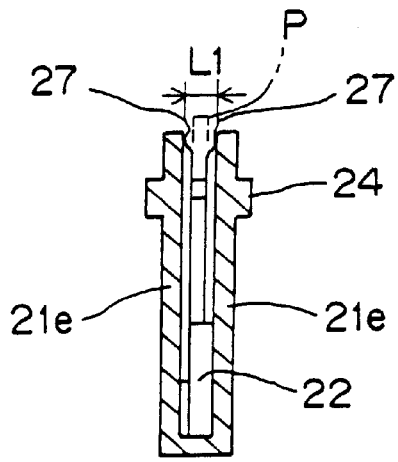
FIG. 6 is a sectional view of the slide glass rack taken along the line VI—VI of FIG. 3.

Referring to FIGS. 5 and 6, the concave 21 has a gap L1 of, for example, 5.0 mm, which is sufficiently larger than the thickness of the slide glass P, and a gap L2 of, for example, 1.6 mm at the longitudinal ends, which is slightly larger than the thickness of the slide glass P. Referring to FIG. 4, in the interior of the concave 21, an arc-shaped surface 21c is formed in a corner portion where the outer surface of the side wall 21a and the outer surface of the bottom wall 21b meet, and an arc-shaped surface 21d is formed in a corner portion where the inner surface of the side wall 21a and the inner surface of the bottom wall 21b meet. The arc-shaped surface 21d is so configured that it deviates outside of lines D that are perpendicular to a direction C in which the centrifugal force is directed. As the arc-shaped surface 21d comes closer to the bottom wall 21b, it deviates more outside with respected to the lines D. With this configuration of the arc-shaped surface 21d, the liquid flows toward the bottom wall 21b when the rack 20 is mounted on the rotor 11 of the centrifugal apparatus 10 and liquid is scattered by the centrifugal force generated by the rotation of the rotor 11.

Two ribs 22 and 23 are formed on the bottom wall 21b of the concave 21. As shown in FIG. 5, the rib 22 is integrally formed with one of the side walls 21e, and the rib 23 is integrally formed with the other of the side walls 21e. Passages 22a and 23a are defined by the respective opposing side walls 21e and 21e.

A flange 24 is formed at the upper portion of the outer peripheral surface of the rack 20. The upper portion of the side wall 21a defining the longitudinal opposing ends of the concave 21 is cut away to form a cut-out portion 25.

As shown in FIG. 4, the upper opening of the side wall 21a defining the concave 21, that is, the longitudinal opposing ends of the concave 21 is chamfered to form a chamfer 26. Also, as shown in FIG. 6, the upper opening of the side wall 21e defining the concave 21, that is, the transversal opposing ends of the concave 21 is chamfered to form a chamfer 27.

In the rack 20 with the above-described configuration, a slide glass P is inserted into the concave 21 through the upper opening. The slide glass P inserted into the concave 21 is shown by a chain double-dashed line in FIG. 4, and the lower edge thereof is supported by the ribs 22 and 23, while the opposing ends thereof are inserted into the gap L2 of the concave 21 as shown in FIG. 5.

Thus, the slide glass P is hold inside the rack 20 with an appropriate gap between its surface excluding the opposing ends and the side wall 21e, and at a position sufficiently above from the bottom wall 21b. As shown in FIG. 4, the opposing ends and the upper peripheral portion of the slide glass P are exposed from the rack 20 when it is held in the rack 20.

Referring to FIG. 2, the rack 20 with the slide glass being mounted therein in the manner as described above is inserted into a hole 14 of the rotor 11. Then, the rack 20 is held with an inclined manner corresponding to the inclination of the inclined portions 11b of the rotor 11.

When the rotor 11 rotates, the water (liquid) attached to the slide glass P is blown off by the centrifugal force, collides against the side wall 21a, arc-shaped surface 21d, etc. of the rack 20, and is guided along the side wall 21a, arc-shaped surface 21d, etc. into the bottom wall 21b where it is accumulated.

When the centrifugal operations are completed, the slide glass P is taken out from the rack 20 in the state where the rack 20 is taken out from the hole 14 of the rotor 11 or it is still mounted in the rotor 11. On that occasion, the slide glass P can easily taken out from the rack 20 by picking with fingers the opposing ends thereof, that is, the portions exposed through the cut-out portions 25 of the rack 20.

In the above embodiment, the arc-shaped surface 21c is formed in a portion where the outer surface of the side wall 21a and the outer surface of the bottom wall 21b meet. Alternatively, this portion may be formed with an inclined surface. Also, in the above embodiment, the arc-shaped surface 21d is formed in a portion where the inner surface of the side wall 21a and the inner surface of the bottom wall 21b meet. Alternatively, this portion may be formed with an inclined surface.

Further, in the above embodiment, the flange 24 is formed in the whole upper peripheral surface of the rack 24.

Alternatively, the flange may be formed only in the longitudinal side surfaces, or only in the longitudinal opposing ends, or in the whole peripheral surface in a discontinuous manner.

What is claimed is:

1. A slide rack, which comprises:

a slide supporting structure which includes a slide accommodating concave that opens upward for supporting a slide, the slide supporting structure including a corner portion where an inner surface of a side wall defining a longitudinal end of the slide supporting structure and an inner surface of a bottom wall of the slide supporting structure meet; and the corner portion has an arc-shaped surface that deviates, toward the bottom wall, outside of a plane that is perpendicular to a direction in which centrifugal force is directed; and a suspension structure for suspending the slide supporting structure within a centrifugal structure which includes a flange provided in an upper outer peripheral surface of the slide supporting structure.

2. A slide rack, which comprises:

a slide supporting structure which includes a slide accommodating concave that opens upward for supporting a slide, the slide supporting structure including a corner portion where an inner surface of a side wall defining a longitudinal end of the rack and an inner surface of a bottom wall of the rack meet; and the corner portion is formed with an inclined plane surface that deviates outside of a plane that is perpendicular to a direction in which centrifugal force is directed; and a suspension structure for suspending the slide rack within a centrifugal structure which includes a flange provided in an upper outer peripheral surface of the slide supporting structure.

* * * * *